United States Patent
Wang et al.

(10) Patent No.: US 11,398,307 B2
(45) Date of Patent: *Jul. 26, 2022

(54) REMOTE CONTROLLED ROBOT SYSTEM THAT PROVIDES MEDICAL IMAGES

(71) Applicant: TELADOC HEALTH, INC.

(72) Inventors: Yulun Wang, Goleta, CA (US); Charles S. Jordan, Santa Barbara, CA (US); Marco Pinter, Goleta, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/464,601

(22) Filed: Aug. 20, 2014

(65) Prior Publication Data

US 2015/0092037 A1 Apr. 2, 2015

Related U.S. Application Data

(63) Continuation of application No. 12/277,842, filed on Nov. 25, 2008, now Pat. No. 8,849,679, which is a
(Continued)

(51) Int. Cl.
*G16H 40/67* (2018.01)
*G06T 7/00* (2017.01)
(Continued)

(52) U.S. Cl.
CPC .......... *G16H 40/67* (2018.01); *G06T 7/0012* (2013.01); *G16H 30/20* (2018.01); *H04N 7/18* (2013.01);
(Continued)

(58) Field of Classification Search
CPC .... G06F 19/3418; G06T 7/0012; H04N 7/185
(Continued)

(56) References Cited

U.S. PATENT DOCUMENTS

| 4,107,689 A | 8/1978 | Jellinek |
| 4,213,182 A | 7/1980 | Eichelberger et al. |

(Continued)

FOREIGN PATENT DOCUMENTS

| CN | 1404695 A | 3/2003 |
| CN | 1561923 A | 1/2005 |

(Continued)

OTHER PUBLICATIONS

Hosford, Christopher; On the Telemedicine Frontier: Dr. Jay Sanders Is Developing Systems Worldwide; South Florida Business Journal 13.7: 3. American City Business Journals. (Oct. 12, 1992) (Year: 1992).*

(Continued)

*Primary Examiner* — Hiep V Nguyen

(57) ABSTRACT

A remote controlled robot system that includes a mobile robot and a remote control station. The mobile robot is controlled by the remote control station and includes a robot monitor, and a robot camera that captures a robot image. The system also includes a medical image device that can be coupled to the robot. The remote control station includes a camera that captures a remote station image, and a monitor that displays the robot image captured by the robot camera in a robot view field, displays the remote station image in a station view field. The robot transmits the robot and medical images to the remote control station such that a larger portion of a network bandwidth is allocated for the medical image than the robot image.

13 Claims, 5 Drawing Sheets

Related U.S. Application Data continuation-in-part of application No. 11/542,605, filed on Oct. 2, 2006, now abandoned, which is a continuation-in-part of application No. 11/455,161, filed on Jun. 15, 2006, now abandoned.

(51) Int. Cl.
  *H04N 7/18* (2006.01)
  *G16H 30/20* (2018.01)
(52) U.S. Cl.
  CPC ... *H04N 7/185* (2013.01); *G06T 2207/10132* (2013.01)
(58) Field of Classification Search
  USPC .......................................................... 705/2
  See application file for complete search history.

(56) References Cited

U.S. PATENT DOCUMENTS

| | | | |
|---|---|---|---|
| 4,553,309 A | 11/1985 | Hess et al. | |
| 4,697,278 A | 9/1987 | Fleischer | |
| 5,220,263 A | 6/1993 | Onishi et al. | |
| 5,262,944 A | 11/1993 | Weisner et al. | |
| 5,400,068 A | 3/1995 | Ishida et al. | |
| 5,617,539 A | 4/1997 | Ludwig et al. | |
| 5,619,341 A | 4/1997 | Auyeung et al. | |
| 5,623,679 A | 4/1997 | Rivette et al. | |
| 5,734,805 A | 3/1998 | Isensee et al. | |
| 5,793,365 A | 8/1998 | Tang et al. | |
| 5,801,755 A | 9/1998 | Echerer | |
| 5,844,599 A | 12/1998 | Hildin | |
| 5,867,494 A | 2/1999 | Krishnaswamy et al. | |
| 5,872,922 A | 2/1999 | Hogan et al. | |
| 6,091,219 A | 7/2000 | Maruo et al. | |
| 6,189,034 B1 | 2/2001 | Riddle | |
| 6,292,714 B1 | 9/2001 | Okabayashi | |
| 6,314,631 B1 | 11/2001 | Pryor | |
| 6,317,953 B1 | 11/2001 | Pryor | |
| 6,373,855 B1 | 4/2002 | Downing et al. | |
| 6,389,329 B1 | 5/2002 | Colens | |
| 6,411,055 B1 | 6/2002 | Fujita et al. | |
| 6,529,620 B2 | 3/2003 | Thompson | |
| 6,567,038 B1 | 5/2003 | Granot et al. | |
| 6,590,604 B1 | 7/2003 | Tucker et al. | |
| 6,597,392 B1 | 7/2003 | Jenkins et al. | |
| 6,667,592 B2 | 12/2003 | Jacobs et al. | |
| 6,674,259 B1 | 1/2004 | Norman et al. | |
| 6,693,585 B1 | 2/2004 | MacLeod | |
| 6,724,823 B2 | 4/2004 | Rovati et al. | |
| 6,816,192 B1 | 11/2004 | Nishikawa | |
| 6,816,754 B2 | 11/2004 | Mukai et al. | |
| 6,893,267 B1 | 5/2005 | Yueh | |
| 6,990,112 B1 | 1/2006 | Brent et al. | |
| 7,011,538 B2 | 3/2006 | Chang | |
| 7,053,578 B2 | 5/2006 | Diehl et al. | |
| 7,055,210 B2 | 6/2006 | Keppler et al. | |
| 7,219,364 B2 | 5/2007 | Bolle et al. | |
| 7,222,000 B2 | 5/2007 | Wang et al. | |
| 7,283,153 B2 | 10/2007 | Provost et al. | |
| 7,292,257 B2 | 11/2007 | Kang et al. | |
| 7,305,114 B2 | 12/2007 | Wolff et al. | |
| 7,332,890 B2 | 2/2008 | Cohen et al. | |
| 7,333,642 B2 | 2/2008 | Green | |
| 7,352,153 B2 | 4/2008 | Yan | |
| 7,363,121 B1 | 4/2008 | Chen et al. | |
| 7,467,211 B1 | 12/2008 | Herman et al. | |
| 7,483,867 B2 | 1/2009 | Ansari et al. | |
| 7,510,428 B2 | 3/2009 | Obata et al. | |
| 7,557,758 B2 | 7/2009 | Rofougaran | |
| 7,587,260 B2 | 9/2009 | Bruemmer et al. | |
| 7,631,833 B1 | 12/2009 | Ghaleb et al. | |
| 7,657,560 B1 | 2/2010 | DiRienzo | |
| 7,703,113 B2 | 4/2010 | Dawson | |
| 7,737,993 B2 | 6/2010 | Kaasila et al. | |
| 7,774,158 B2 | 8/2010 | Domingues Goncalves et al. | |
| 7,861,366 B2 | 1/2011 | Hahm et al. | |
| 7,885,822 B2 | 2/2011 | Akers et al. | |
| 7,956,894 B2 | 6/2011 | Akers et al. | |
| 7,957,837 B2 | 6/2011 | Ziegler et al. | |
| 7,982,769 B2 | 7/2011 | Jenkins et al. | |
| 8,126,960 B2 | 2/2012 | Obradovich et al. | |
| 8,212,533 B2 | 7/2012 | Ota | |
| 8,287,522 B2 | 10/2012 | Moses et al. | |
| 8,320,534 B2 | 11/2012 | Kim et al. | |
| 8,348,675 B2 | 1/2013 | Dohrmann | |
| 8,374,171 B2 | 2/2013 | Cho et al. | |
| 8,400,491 B1 | 3/2013 | Panpaliya et al. | |
| 8,401,275 B2 | 3/2013 | Wang et al. | |
| 8,423,284 B2 | 4/2013 | O'Shea | |
| 8,451,731 B1 | 5/2013 | Lee et al. | |
| 8,515,577 B2 | 8/2013 | Wang et al. | |
| 8,610,786 B2 | 12/2013 | Ortiz | |
| 8,612,051 B2 | 12/2013 | Norman et al. | |
| 8,639,797 B1 | 1/2014 | Pan et al. | |
| 8,670,017 B2 | 3/2014 | Stuart et al. | |
| 8,726,454 B2 | 5/2014 | Gilbert et al. | |
| 8,836,751 B2 | 9/2014 | Ballantyne et al. | |
| 8,849,679 B2 | 9/2014 | Wang et al. | |
| 8,849,680 B2 | 9/2014 | Wright et al. | |
| 8,861,750 B2 | 10/2014 | Roe et al. | |
| 8,897,920 B2 | 11/2014 | Wang et al. | |
| 8,902,278 B2 | 12/2014 | Pinter et al. | |
| 2002/0044201 A1 | 4/2002 | Alexander et al. | |
| 2002/0106998 A1 | 8/2002 | Presley et al. | |
| 2002/0109775 A1 | 8/2002 | White et al. | |
| 2002/0128985 A1 | 9/2002 | Greenwald | |
| 2003/0080901 A1 | 5/2003 | Piotrowski | |
| 2003/0112823 A1 | 6/2003 | Collins et al. | |
| 2003/0120714 A1 | 6/2003 | Wolff et al. | |
| 2003/0135097 A1 | 7/2003 | Wiederhold et al. | |
| 2003/0195662 A1 | 10/2003 | Wang et al. | |
| 2003/0216833 A1 | 11/2003 | Mukai et al. | |
| 2004/0008138 A1 | 1/2004 | Hockley, Jr. et al. | |
| 2004/0017475 A1 | 1/2004 | Akers et al. | |
| 2004/0019406 A1* | 1/2004 | Wang | B25J 5/007 700/231 |
| 2004/0088078 A1 | 5/2004 | Jouppi et al. | |
| 2004/0117067 A1 | 6/2004 | Jouppi | |
| 2004/0150725 A1 | 8/2004 | Taguchi | |
| 2004/0168148 A1 | 8/2004 | Goncalves et al. | |
| 2004/0218099 A1 | 11/2004 | Washington | |
| 2004/0260790 A1 | 12/2004 | Balloni et al. | |
| 2005/0024485 A1* | 2/2005 | Castles | H04N 7/147 348/14.03 |
| 2005/0052527 A1* | 3/2005 | Remy | H04N 7/181 348/14.08 |
| 2005/0073575 A1 | 4/2005 | Thacher et al. | |
| 2005/0125083 A1 | 6/2005 | Kiko | |
| 2005/0149364 A1* | 7/2005 | Ombrellaro | A61B 5/103 705/3 |
| 2005/0152447 A1 | 7/2005 | Jouppi et al. | |
| 2005/0152565 A1 | 7/2005 | Jouppi et al. | |
| 2005/0168568 A1 | 8/2005 | Jouppi | |
| 2005/0264649 A1 | 12/2005 | Chang et al. | |
| 2005/0286759 A1 | 12/2005 | Zitnick et al. | |
| 2006/0010028 A1 | 1/2006 | Sorensen | |
| 2006/0056655 A1 | 3/2006 | Wen et al. | |
| 2006/0056837 A1 | 3/2006 | Vapaakoski | |
| 2006/0066609 A1 | 3/2006 | Iodice et al. | |
| 2006/0071797 A1 | 4/2006 | Rosenfeld et al. | |
| 2006/0178559 A1 | 8/2006 | Kumar et al. | |
| 2007/0093279 A1 | 4/2007 | Janik | |
| 2007/0116152 A1 | 5/2007 | Thesling | |
| 2007/0170886 A1 | 7/2007 | Plishner | |
| 2007/0226949 A1 | 10/2007 | Hahm et al. | |
| 2007/0290040 A1 | 12/2007 | Wurman et al. | |
| 2008/0027591 A1 | 1/2008 | Lenser et al. | |
| 2008/0033641 A1 | 2/2008 | Medalia | |
| 2008/0051985 A1 | 2/2008 | D'Andrea et al. | |
| 2008/0086241 A1 | 4/2008 | Phillips et al. | |
| 2008/0091340 A1 | 4/2008 | Milstein et al. | |
| 2008/0161969 A1 | 7/2008 | Lee et al. | |
| 2008/0232763 A1 | 9/2008 | Brady | |

(56) References Cited

U.S. PATENT DOCUMENTS

| | | | |
|---|---|---|---|
| 2008/0263628 | A1 | 10/2008 | Norman et al. |
| 2008/0267069 | A1 | 10/2008 | Thielman et al. |
| 2009/0049640 | A1 | 2/2009 | Lee et al. |
| 2009/0102919 | A1 | 4/2009 | Zamierowski et al. |
| 2010/0017046 | A1 | 1/2010 | Cheung et al. |
| 2010/0026239 | A1 | 2/2010 | Li et al. |
| 2010/0030578 | A1 | 2/2010 | Siddique et al. |
| 2010/0066804 | A1 | 3/2010 | Shoemake et al. |
| 2010/0171826 | A1 | 7/2010 | Hamilton et al. |
| 2010/0278086 | A1 | 11/2010 | Pochiraju et al. |
| 2010/0286905 | A1 | 11/2010 | Goncalves et al. |
| 2010/0301679 | A1 | 12/2010 | Murray et al. |
| 2011/0022705 | A1 | 1/2011 | Yellamraju et al. |
| 2011/0071675 | A1 | 3/2011 | Wells et al. |
| 2011/0072114 | A1 | 3/2011 | Hoffert et al. |
| 2011/0153198 | A1 | 6/2011 | Kokkas et al. |
| 2011/0193949 | A1 | 8/2011 | Nambakam et al. |
| 2011/0195701 | A1 | 8/2011 | Cook et al. |
| 2011/0280551 | A1 | 11/2011 | Sammon |
| 2011/0306400 | A1 | 12/2011 | Nguyen |
| 2012/0059946 | A1 | 3/2012 | Wang |
| 2012/0113856 | A1 | 5/2012 | Krishnaswamy |
| 2012/0203731 | A1 | 8/2012 | Nelson et al. |
| 2012/0291809 | A1 | 11/2012 | Kuhe et al. |
| 2013/0250938 | A1 | 9/2013 | Anandakumar et al. |
| 2014/0047022 | A1 | 2/2014 | Chan et al. |
| 2014/0085543 | A1 | 3/2014 | Hartley et al. |
| 2014/0135990 | A1 | 5/2014 | Stuart et al. |
| 2014/0139616 | A1 | 5/2014 | Pinter et al. |
| 2014/0155755 | A1 | 6/2014 | Pinter et al. |

FOREIGN PATENT DOCUMENTS

| | | | | |
|---|---|---|---|---|
| CN | 1743144 | A | 3/2006 | |
| CN | 101049017 | A | 10/2007 | |
| CN | 101151614 | A | 3/2008 | |
| CN | 100407729 | C | 7/2008 | |
| JP | 11220706 | A | 8/1999 | |
| JP | 2002321180 | A | 11/2002 | |
| JP | 2004181229 | A | 7/2004 | |
| JP | 2005111083 | A | 4/2005 | |
| JP | 2009125133 | A | 6/2009 | |
| WO | 9742761 | A1 | 11/1997 | |
| WO | 2008100272 | A2 | 8/2008 | |
| WO | WO-2011028589 | A2 * | 3/2011 | ......... G06F 19/3418 |

OTHER PUBLICATIONS

Fulbright et al., "SWAMI: An Autonomous Mobile Robot for Inspection of Nuclear Waste of Storage Facilities", Autonomous Robots, vol. 2, 1995, pp. 225-235.
Screenshot Showing Google Date for Lemaire Telehealth Manual, Screenshot Retrieved on Dec. 18, 2014, 1 page.
Nomadic Technologies, Inc., "Nomad Scout Language Reference Manual", Software Version: 2.7, Part No. DOC00002, Jul. 12, 1999, 47 pages.
"Appeal from the U.S. District Court for the Central District of California in No. 11-CV-9185, Judge Percy Anderson", May 9, 2014, pp. 1-48.
"Google translation of: Innovations Report", From research project to television star: Care-O-bot in ZDF series, http://www.innovations-report.de/specials/printa.php?id=5157, Sep. 28, 2001, 2 pages.
"MPEG File Format Summary", downloaded from: http://www.fileformat.info/format/mpeg/egff.htm, Feb. 1, 2001, 8 pages.
"Nomad Scout User's Manual", Nomadic Technologies, Software Version 2. 7, Part No. DOC00004, Jul. 12, 1999, pp. 1-59.
ACM Digital Library Record, "Autonomous Robots vol. 11 Issue 1", downloaded from <http://dl.acm.org/citation.cfm?id=591550&picked=prox&cfid=360891374&cftoken=35225929>, Jul. 2001, 2 pages.
Bartholomew, "Pharmacy Apothecary", available online at<http://classes.bnf.fr/ema/grands/034.htm>, retrived on Jul. 26, 2012.
Brenner, "A technical tutorial on the IEEE 802.11 protocol", BreezeCOM Wireless Communications, 1997, pp. 1-24.
CMU Course 16X62, "Robot user's manual", (describing the Nomad Scout), Carnegie Mellon University, Feb. 1, 2001, 11 pages.
Ellison, et al., "Telerounding and Patient Satisfaction Following Surgery", 523-530.
Ishiguro, et al., "Integrating a Perceptual Information Infrastructure with Robotic Avatars: A Framework for Tele-Existence", Intelligent Robots and Systems, 1999. IROS '99. Proceedings. 1999 IEEE/RSJ International Conference, vol. 2, 1999, pp. 1032-1038.
Ivanova, "Master's thesis: Internet Based Interface for Control of a Mobile Robot", Department of Numerical Analysis and Computer Science, 2003, 59 pages.
Kaplan, et al., "An Internet Accessible Telepresence", Multimedia Systems Journal, vol. 5, 1996, 7 pages.
Koenen, "MPEG-4: a Powerful Standard for Use in Web and Television Environments", (KPN Research), downloaded from http://www.w3.org/Architecture/1998/06/Workshop/paper26, Jul. 1, 1998, 4 pages.
Kuzuoka, et al., "Can the GestureCam be a Surrogate?", Proceedings of the Fourth European Conference on Computer-Supported Cooperative Work, 1995, pp. 181-196.
Library of Congress, "008—Fixed-Length Data Elements (NR)", MARC 21 Format for Classification Data, downloaded from http://www.loc.gov/marc/classification/cd008.html, Jan. 2000, pp. 1-14.
Panusopone, et al., "Performance comparison of MPEG-4 and H.263+ for streaming video applications", Circuits Systems Signal Processing, vol. 20, No. 3, 2001, pp. 293-309.
Paulos, et al., "Personal Tele-Embodiment", Chapter 9 in Goldberg, et al., ed. "Beyond webcams", MIT Press, Jan. 4, 2002, pp. 155-167.
Paulos, "Personal tele-embodiment", OskiCat Catalog Record, UCB Library Catalog, 2001, 3 pages.
Paulos, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages, including 4 pages of e-mails.
Paulos, et al., "Social Tele-Embodiment: Understanding Presence", Autonomous Robots, vol. 11, Issue 1, Kluwer Academic Publishers, Jul. 2001, pp. 87-95.
Schraft, et al., "Care-O-bot™: the concept of a system fro assisting elderly or disabled persons in home enviornments", IEEE Proceedings of the 24th Annual Conference of the Industrial Electronics Society, IECON '98, Aug.31-Sep. 4, 1998, pp. 2476-2481.

* cited by examiner

REMOTE CONTROLLED ROBOT SYSTEM THAT PROVIDES MEDICAL IMAGES

CROSS-REFERENCE TO RELATED APPLICATION

This application is a continuation-in-part of U.S. application Ser. No. 11/542,605, filed on Oct. 2, 2006, pending, which is as a continuation-in-part of U.S. application Ser. No. 11/455,161, filed on Jun. 15, 2006.

BACKGROUND OF THE INVENTION

1. Field of the Invention

The subject matter disclosed generally relates to the field of mobile two-way teleconferencing.

2. Background Information

There has been marketed a mobile robot introduced by InTouch Technologies, Inc., the assignee of this application, under the trademarks COMPANION, RP-6 and RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

The InTouch robot can be used by medical personnel to monitor and interact with a patient. For example, a doctor can move the robot into a patient's room and utilize the two-way videoconferencing capabilities of the system to examine the patient. Examination of the patient is limited to visual inspection and audio feedback. It would be desirable if the system would also allow other devices to be used to examine and interact with a patient.

BRIEF SUMMARY OF THE INVENTION

A remote controlled robot system that includes a mobile robot and a remote control station. The mobile robot is controlled by the remote control station and includes a robot monitor, and a robot camera that captures a robot image. The system also includes a medical image device that can be coupled to the robot. The remote control station includes a camera that captures a remote station image, and a monitor that displays the robot image captured by the robot camera in a robot view field, displays the remote station image in a station view field. The robot transmits the robot and medical images to the remote control station such that a larger portion of a network bandwidth is allocated for the medical image than the robot image.

DETAILED DESCRIPTION

Disclosed is a remote controlled robot system that includes a mobile robot and a remote control station. The mobile robot is controlled by the remote control station and includes a robot monitor, and a robot camera that captures a robot image. The system also includes a medical image device that can be coupled to the robot. The remote control station includes a camera that captures a remote station image, and a monitor that displays the robot image captured by the robot camera in a robot view field, displays the remote station image in a station view field. The robot transmits the robot and medical images to the remote control station such that a larger portion of a network bandwidth is allocated for the medical image than the robot image. A medical personnel at the remote control station can interact with another personnel at the robot site to move the medical image device to vary the captured images. The system allows the remote operator to conduct a video conference with someone at the robot site while viewing medical images in real time.

Figure 1:
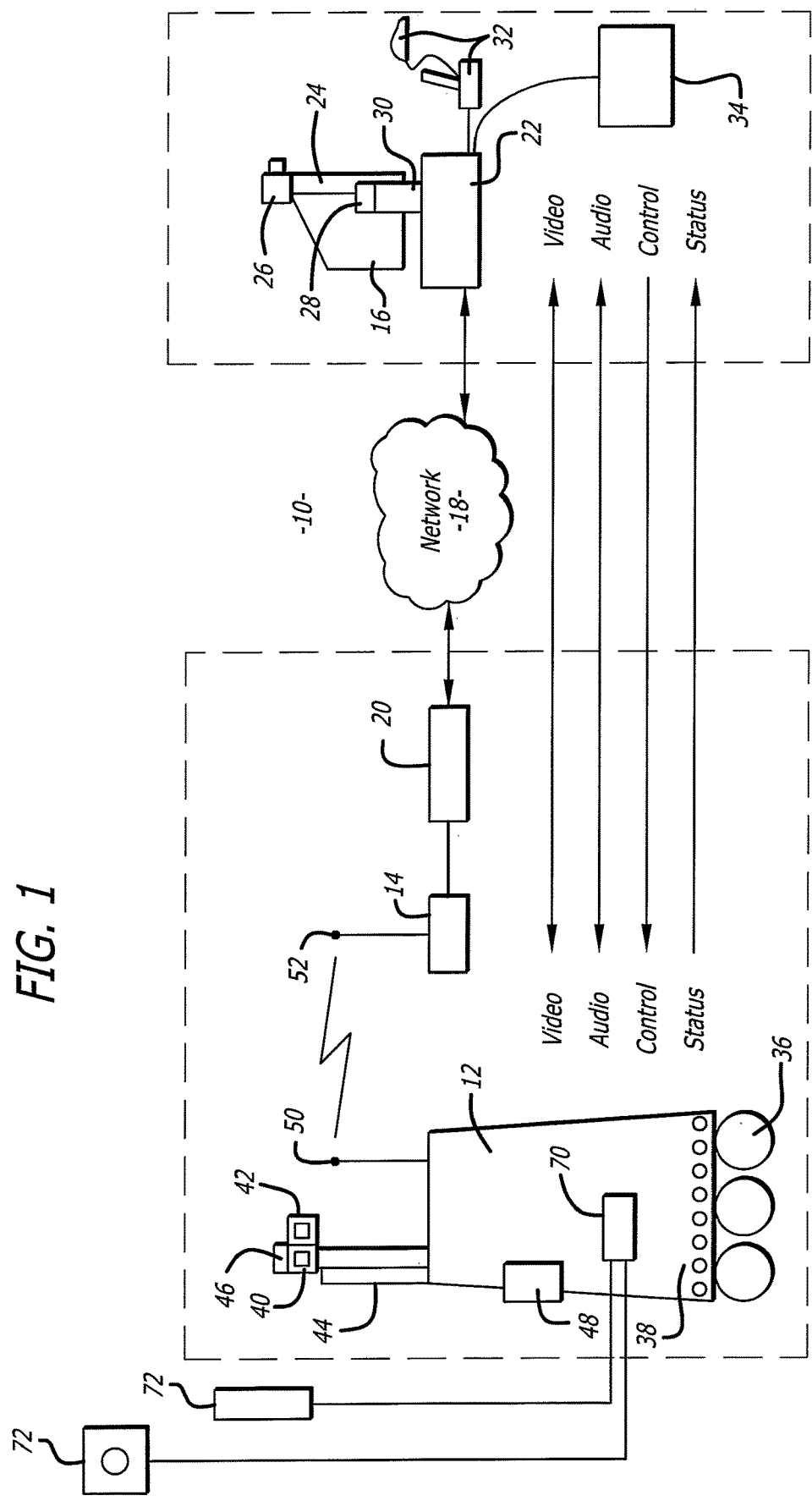
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick and/or a mouse and a keyboard 34. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 36 that is attached to a robot housing 38. Also attached to the robot housing 36 is a pair of cameras 40 and 42, a monitor 44, a microphone(s) 46 and a speaker(s) 48. The microphone 46 and speaker 30 may create a stereophonic sound. The robot 12 may also have an antenna 50 that is wirelessly coupled to an antenna 52 of the base station 14. The robot monitor 44 and cameras 40 and 82 move together in two degrees of freedom including pan and tilt directions. The system 10 allows a user at the remote control station 16 to move the robot 12 through operation of the input device 32. The robot cameras 40 and 42 are coupled to the remote monitor 24 so that a user at the remote station 16 can view a patient. Likewise, the robot monitor 44 is coupled to the remote camera 26 so that the patient can view the user. The microphones 28 and 46, and speakers 30 and 48, allow for audible communication between the patient and the user.

Camera 40 may provide a wide angle view. Conversely, camera 42 may contain a zoom lens to provide a narrow angle view. Camera 42 can capture a zoom image that is transmitted to the remote control station. Camera 40 can capture a non-zoom image that can be transmitted to the remote control station. Although two cameras are shown and described, it is to be understood that the robot may contain only one camera that has the capability to provide a zoom image and a non-zoom image.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The robot 12 may include an auxiliary video port 70. The auxiliary video port 70 may include USB, VGA, Y-video/audio electrical connectors and associated electronic circuitry. A plurality of video devices 72 can be connected to one or more of the ports 70. By way of example, the video devices 72 may include an ultrasound device, an otoscope, a echocardiogram, a dermatology camera, a ceiling camera and/or a video playback machine such as a VCR or DVD player. The video devices 72 capture video that is transmitted to the remote station 16 through the mobile robot 12. By way of example, the ultrasound device may capture images of a patient that are then transmitted to the remote control station 16 and displayed by the station monitor 24. The video devices 72 can be coupled to the robot with either a wire or through a wireless connection. For purposes of this patent an auxiliary port will describe both wireless and wired connections between a video device and the robot.

Figure 2:
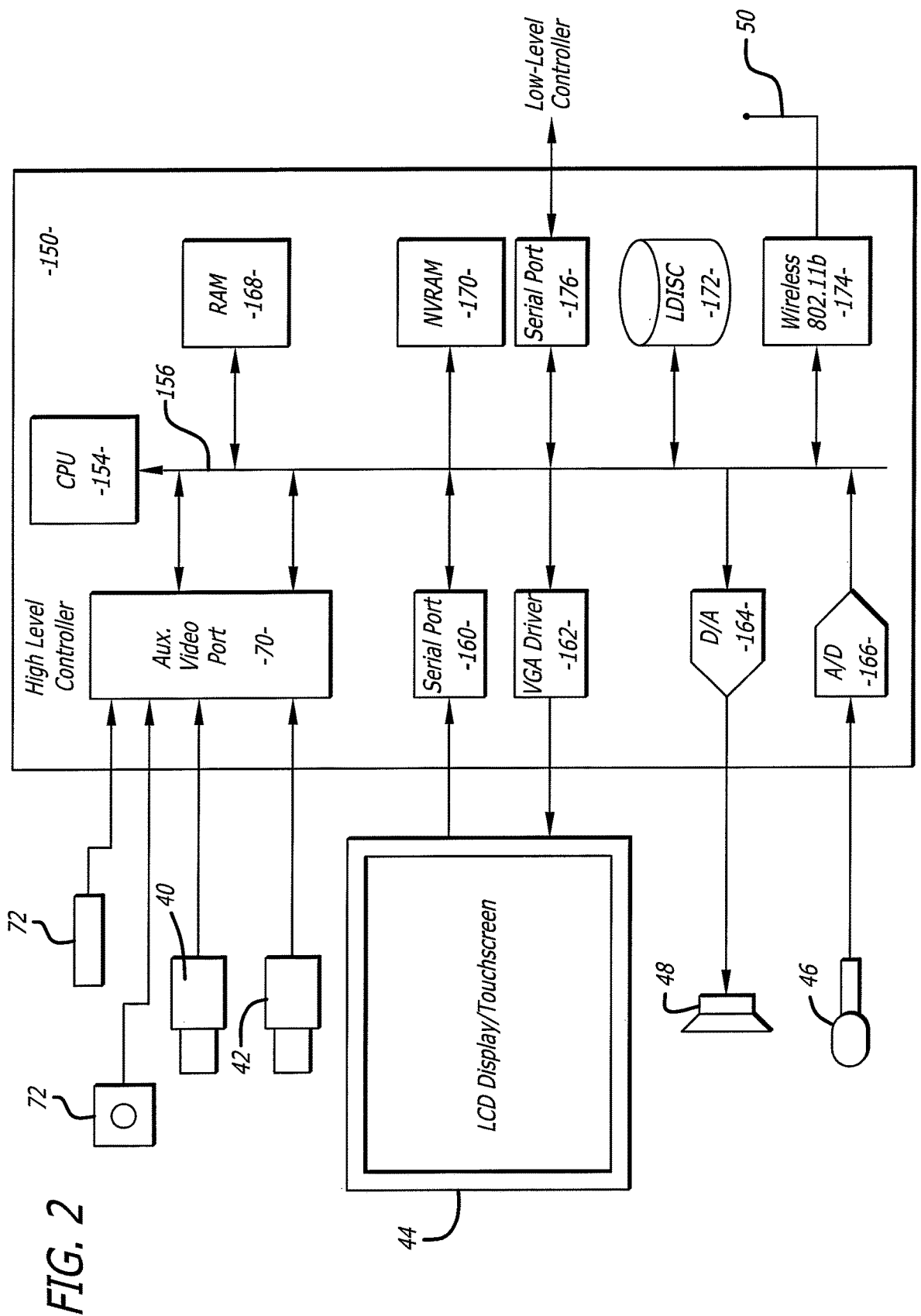
FIG. 2 is a schematic of an electrical system of a robot.
Figure 3:
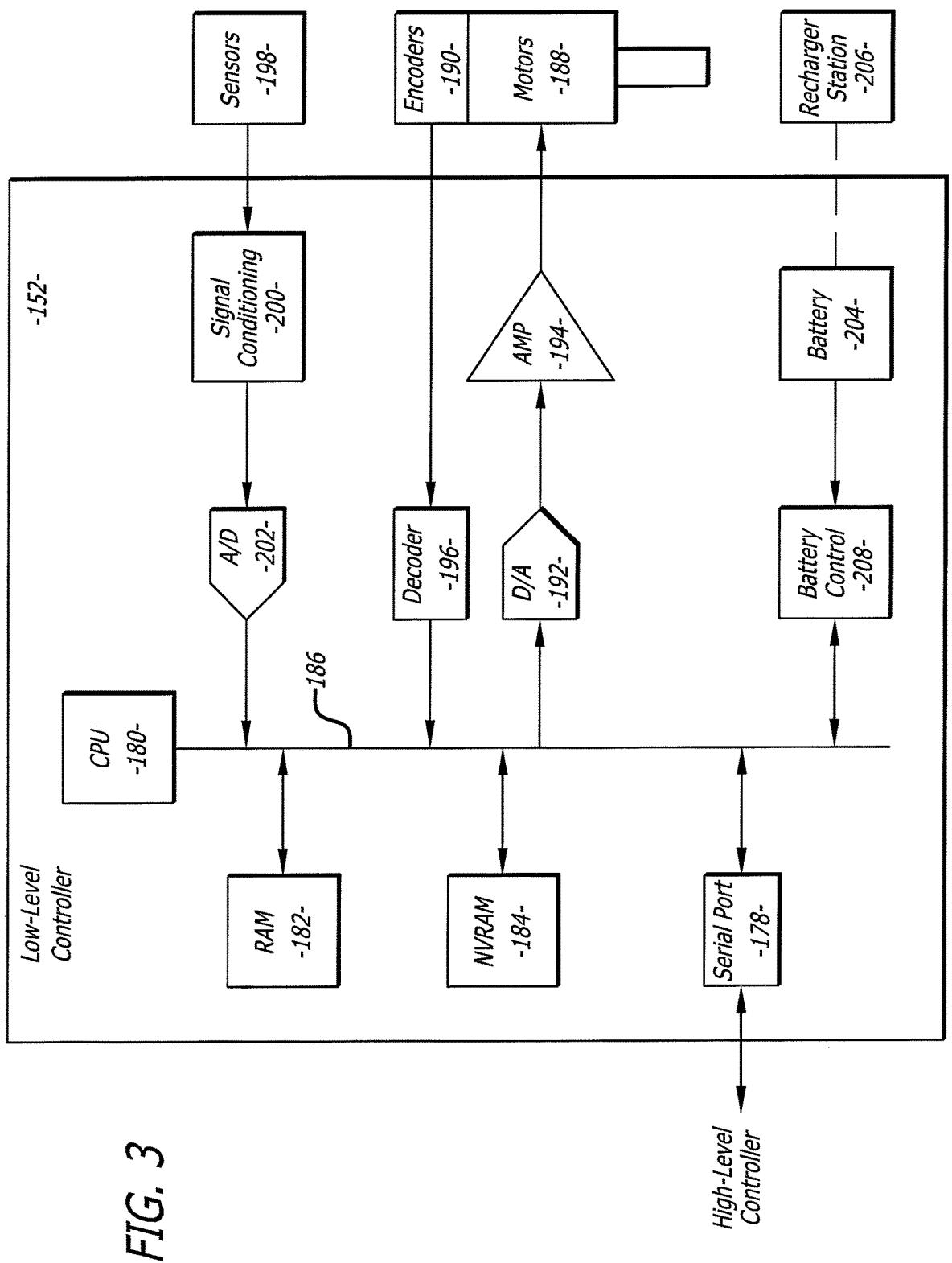
FIG. 3 is a further schematic of the electrical system of the robot.

FIGS. 2 and 3 show an embodiment of a robot 12. Each robot 12 may include a high level control system 150 and a low level control system 152. The high level control system 150 may include a processor 154 that is connected to a bus 156. The auxiliary video port 70 is coupled to the robot cameras 40 and 42 and the external video devices 72. The port 70 may include a frame grabber that has multiple composite video inputs that allow the robot to capture video from the cameras 40 and 42 and the video devices 72. The port 70 provides video from one of the video devices, or cameras 40 or 42, based on input from the remote control station 16. For, example, the port 70 may feed video from camera 40 and then switch the feed to one of the video devices 72.

The monitor 44 is coupled to the bus 156 by a serial output port 160 and a VGA driver 162. The monitor 44 may include a touchscreen function that allows the patient to enter input by touching the monitor screen.

The speaker 48 is coupled to the bus 156 by a digital to analog converter 164. The microphone 46 is coupled to the bus 156 by an analog to digital converter 166. The high level controller 150 may also contain random access memory (RAM) device 168, a non-volatile RAM device 170 and a mass storage device 172 that are all coupled to the bus 156. The mass storage device 172 may contain medical files of the patient that can be accessed by the user at the remote control station 16. For example, the mass storage device 172 may contain a picture of the patient. The user, particularly a health care provider, can recall the old picture and make a side by side comparison on the monitor 24 with a present video image of the patient provided by the camera 40. The robot antennae 50 may be coupled to a wireless transceiver 174. By way of example, the transceiver 174 may transmit and receive information in accordance with IEEE 802.11b.

The controller 154 may operate with a LINUX OS operating system. The controller 154 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 150 operates to control communication between the robot 12 and the remote control station 16.

The remote control station 16 may include a computer that is similar to the high level controller 150. The computer would have a processor, memory, I/O, software, firmware, etc. for generating, transmitting, receiving and processing information.

The high level controller 150 may be linked to the low level controller 152 by serial ports 176 and 178. The low level controller 152 includes a processor 180 that is coupled to a RAM device 182 and non-volatile RAM device 184 by a bus 186. Each robot 12 contains a plurality of motors 188 and motor encoders 190. The motors 188 can actuate the movement platform and move other parts of the robot such as the monitor and camera. The encoders 190 provide feedback information regarding the output of the motors 188. The motors 188 can be coupled to the bus 186 by a digital to analog converter 192 and a driver amplifier 194. The encoders 190 can be coupled to the bus 186 by a decoder 196. Each robot 12 also has a number of proximity sensors 198 (see also FIG. 1). The position sensors 198 can be coupled to the bus 186 by a signal conditioning circuit 200 and an analog to digital converter 202.

The low level controller 152 runs software routines that mechanically actuate the robot 12. For example, the low level controller 152 provides instructions to actuate the movement platform to move the robot 12. The low level controller 152 may receive movement instructions from the high level controller 150. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 204. The battery 204 may be recharged by a battery recharger station 206 (see also FIG. 1). The low level controller 152 may include a battery control circuit 208 that senses the power level of the battery 204. The low level controller 152 can sense when the power falls below a threshold and then send a message to the high level controller 150.

The system 10 may be the same or similar to a robotic system provided by the assignee InTouch-Health, Inc. of Santa Barbara, Calif. under the name RP-6 or RP-7. The system may also be the same or similar to the system disclosed in U.S. Pat. No. 6,925,357 issued to Wang et al. on Aug. 2, 2005, which is hereby incorporated by reference.

Figure 4:
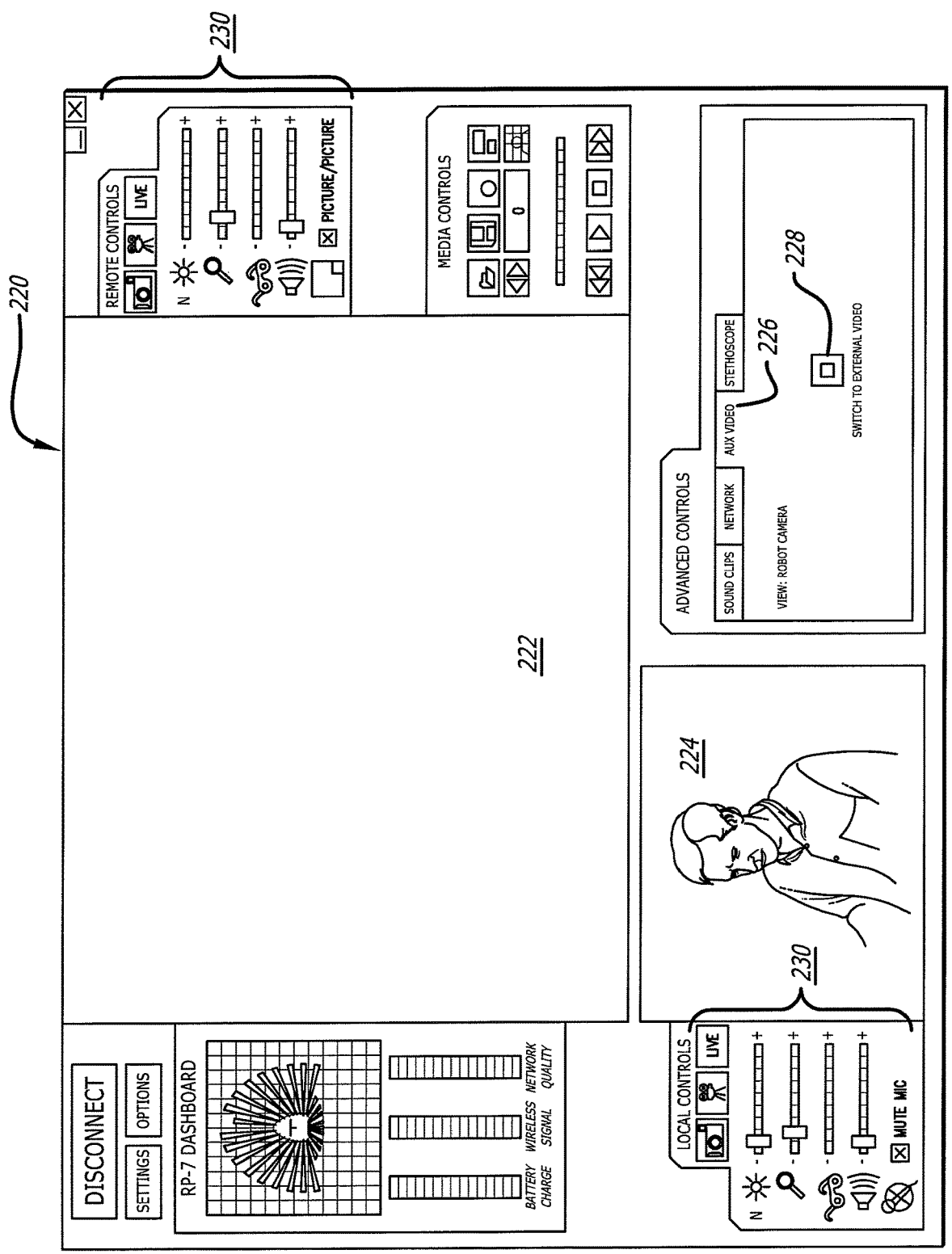
FIG. 4 is a graphical user interface of a remote station.

FIG. 4 shows a display user interface ("DUI") 220 that can be displayed at the remote station 16. The DUI 220 may include a robot view field 222 that displays a video image provided by one of the cameras 40 or 42, or one of the video devices 72 at the robot location. The DUI 220 may include a station view field 224 that displays a video image provided by the camera of the remote station 16. The DUI 220 may be part of an application program stored and operated by the computer 22 of the remote station 16.

The display user interface 220 may include a Aux Video graphical tab 226 that display a button 228. The button 228 can be selected by a user to display video provided by one of the video devices 72 in the robot view field 222. The interface 220 may have additional graphical icons 230 that allow the user to adjust different parameters of the system such as camera brightness, audio volume, capturing a still picture, etc.

The user can highlight a portion of a non-zoom image to display a zoom image that corresponds to the highlighted area. Additionally, the user can circle, annotate, etc. portions of video with a telestrator function of the system 10.

Figure 5:
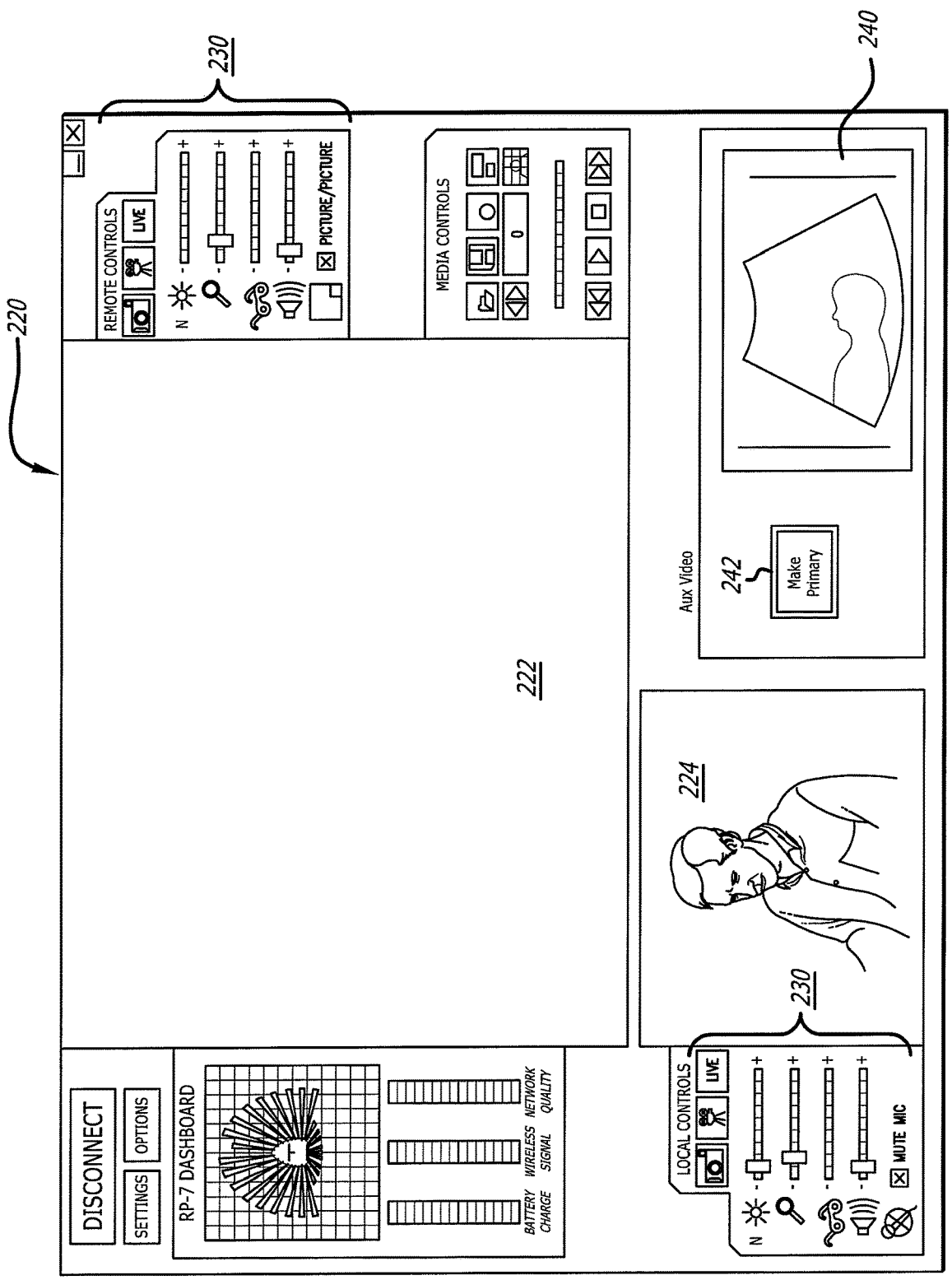
FIG. 5 is the graphical user interface showing a medical image in an auxiliary view field.

The system 10 can be used in a process wherein a medical personnel such as a doctor move the robot 12 adjacent to a patient that is being assisted by another medical personnel such as a nurse. The nurse can plug the ultrasound device into the auxiliary video port of the robot. Plugging the ultrasound device into the robot may cause ultrasound images to be transmitted and displayed within the robot view field 222. Alternatively, the doctor can select graphical button 228 which causes the ultrasound image to be displayed in an auxiliary view field 240 shown in FIG. 5. The auxiliary field 240 may have a graphical button 242 that can be selected to switch the ultrasound image into the robot view field 222 and the images from the robot camera into field 240. When both ultrasound and video images from the robot camera are transmitted to the remote station, the robot may enter a mode wherein the ultrasound images are transmitted at a larger frame size, higher frame rate and higher video compression and the robot camera images are transmitted at a smaller frame size, lower frame rate and lower compression. This mode allocates a higher portion of network bandwidth to the medical images. This mode can be selected through a graphical button (not shown) displayed on the remote control station monitor. The robot camera images and the medical images may also be encrypted. For example, the images may be encrypted with a 128 bit AES encryption with a symmetric key that is exchanged at the start of a session.

During a session where an ultrasound device is coupled to the robot a technician may be located at the robot site in the vicinity of a patient. The technician may move the ultrasound device to different positions on the patient. The images are transmitted to the control station and displayed by the monitor for viewing by a doctor. The doctor and technician can discuss the ultrasound images through the control station and robot. The doctor may also provide instructions on where to place the ultrasound device. For example, the doctor can instruct the technician to move the ultrasound device to different locations on a patient. The system allows the doctor to conduct a remote video conference while viewing ultrasound images in real time.

The robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or a facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 150.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
| --- | --- | --- | --- | --- | --- |
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
| --- | --- | --- | --- | --- | --- | --- |
| | | Local | Caregiver | Doctor | Family | Service |
| Current User | Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |

TABLE II-continued

| | Requesting User | | | | |
|---|---|---|---|---|---|
| | Local | Caregiver | Doctor | Family | Service |
| Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| Control Commands | | |
|---|---|---|
| Command | Example | Description |
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |

TABLE III-continued

| Control Commands | | |
|---|---|---|
| Command | Example | Description |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

| Reporting Commands | | |
|---|---|---|
| Command | Example | Description |
| abnormalExit | abnormalExit | This message informs the user that the robot software has crashed or otherwise exited abnormally. Te robot software catches top-level exceptions and generates this message if any such exceptions occur. |

TABLE IV-continued

Reporting Commands

| Command | Example | Description |
|---|---|---|
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

The processor 154 of the robot high level controller 150 may operate a program that determines whether the robot 12 has received a robot control command within a time interval. For example, if the robot 12 does not receive a control command within 2 seconds then the processor 154 provides instructions to the low level controller 150 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical teleconferencing system, comprising:
a teleconferencing device at a first location and in the vicinity of a patient, the teleconferencing device having a monitor, a camera that captures video of a patient, an auxiliary video port, a microphone, and a speaker;
a medical image device at the first location, the medical image device is coupled to said auxiliary video port and captures medical video of the patient; and,
a remote control station at a second location that is remote from the first location, the remote control station is coupled to the teleconferencing device via a network and includes a station camera that captures provider video of a medical provider located at the second location and a station monitor that displays a display user interface, said display user interface simultaneously displays the patient video captured by said teleconferencing device camera in a remote view field, said provider video in a station view field, and a graphical input that, when selected, causes the display user interface to simultaneously display said medical video in an auxiliary view field along with the patient video and the provider video, wherein the medical provider can control the teleconferencing device via an input device of the remote control station and conduct a video conference with personnel in the vicinity of the teleconferencing device while viewing the patient video and the medical video.

2. The system of claim 1, wherein said medical image device is an ultrasound device.

3. The system of claim 1, wherein said medical image device is an otoscope.

4. The system of claim 1, wherein said medical image device is an echocardiogram.

5. The system of claim 1, wherein said camera and said monitor of the teleconferencing device are mechanically coupled to always move together.

6. The system of claim 1, wherein a larger portion of a network bandwidth is allocated for the medical video than the patient video.

7. The system of claim 1, wherein the medical provider controls the camera of the videoconferencing device via the input device of the remote station.

8. The system of claim 7, wherein controlling the camera of the teleconference device includes controlling at least one of a pan, a tilt, or a zoom of the camera.

9. A method for reviewing images of a patient, comprising:
controlling a teleconferencing device at a first location and in the vicinity of a patient via an input device of a remote control station at a second location remote from the first location, each of the teleconferencing device and the remote control station includes a microphone, a speaker, a camera, and a monitor;
capturing patient video of the patient with the camera of the teleconferencing device;
transmitting the patient video to the remote control station via a network;
displaying the patient video on the remote control station monitor;
moving a medical image device relative to the patient by medical personnel in the vicinity of the patient;
capturing medical video of the patient with the medical image device, the captured medical video being provided to the teleconferencing device;
transmitting the medical video from the teleconferencing device to the remote control station via the network;
capturing provider video of a medical provider at the second location with the remote control station camera;
displaying a display user interface that simultaneously displays the patient video, the provider video, and a graphical input that, when selected, causes the display user interface to simultaneously display the medical video along with the patient video and the station video;
receiving a selection of the graphical input via the input device of the remote control station;
displaying the medical video on the display user interface of the remote control station monitor simultaneously with the display of the patient video and the provider video; and,
conducting a video conference between the medical personnel and the medical provider while the medical provider views the medical video and the patient video.

10. The method of claim 9, wherein the medical image device captures ultrasound images.

11. The method of claim 9, wherein the medical video is transmitted at a higher frame rate than the patient video.

12. The method of claim 9, wherein controlling the teleconferencing device via the input device of the remote station includes controlling the camera of the teleconferencing device.

13. The method of claim 12, wherein controlling the camera of the teleconferencing device includes controlling at least one of a pan, a tilt, or a zoom of the camera.

* * * * *